United States Patent [19]

Hope et al.

[11] Patent Number: 5,785,987
[45] Date of Patent: Jul. 28, 1998

[54] METHOD FOR LOADING LIPID VESICLES

[75] Inventors: Michael Hope; Pieter R. Cullis, both of Vancouver; David B. Fenske, Surrey; Kim F. Wong, Vancouver, all of Canada

[73] Assignee: The University of British Columbia, Canada

[21] Appl. No.: 607,614

[22] Filed: Feb. 27, 1996

Related U.S. Application Data

[63] Continuation-in-part of Ser. No. 399,692, Feb. 27, 1995.
[51] Int. Cl.[6] ........................................... A61K 9/127
[52] U.S. Cl. .................................... 424/450; 264/4.1
[58] Field of Search ............................ 424/450; 264/4.1, 264/4.3

[56] References Cited

FOREIGN PATENT DOCUMENTS 9300888  1/1993  WIPO .

*Primary Examiner*—Gollamudi S. Kishore
*Attorney, Agent, or Firm*—Townsend and Townsend and Crew LLP

[57] ABSTRACT

Methods for the preparation of stable liposome formulations of protonatable therapeutic agents. The methods involve loading a therapeutic agent into preformed liposomes having a methylamine concentration gradient across the lipid bilayer of the liposomes. These methods provide liposome formulations which are more stable, more cost effective, and easier to prepare in a clinical environment than those previously available. The present invention also provides the pharmaceutical compositions prepared by the above methods, a kit for the preparation of liposome formulations of therapeutic agents, and methods for their use.

12 Claims, 11 Drawing Sheets

DOXORUBICIN

CIPROFLOXACIN

- UNCOUPLED LIPOSOMES (NO SERUM)
- UNCOUPLED LIPOSOMES INCUBATED IN 50% MOUSE SERUM
- NRLu-10 COUPLED LIPOSOMES INCUBATED IN 50% MOUSE SERUM

METHOD FOR LOADING LIPID VESICLES

This application is a continuation-in-part of 08/399,692 filed Feb. 27, 1995, now pending.

FIELD OF THE INVENTION

This invention relates to a method for the preparation of liposome formulations of pharmaceutical compounds, and in particular to the liposome formulations incorporating compounds bearing an amino group. This method avoids conditions and procedures which are detrimental to the lipids and/or therapeutic agents or substances to be encapsulated therein. More importantly, the present invention provides methods having broader applicability than has been demonstrated or described for previously known methods.

BACKGROUND OF THE INVENTION

Liposomes, or lipid vesicles, are a recognized drug delivery system which can improve the therapeutic activity and increase the safety of a number of different pharmaceutical agents. To be useful in medical treatments, liposome formulations should have an efficient drug to lipid ratio, a practical shelf-life and be capable of reproducible preparation. High drug to lipid ratios reduce the non-therapeutic lipid "load" to the patient, and also lowers the cost of manufacture, since less pharmaceutical is lost in the process of manufacture.

Liposomal carrier systems (vesicles) are microscopic spheres of one or more lipid bilayers arranged concentrically around an aqueous core. The vesicles have been shown to be suitable as carriers for both hydrophilic and hydrophobic therapeutic agents owing to their unique combination of lipophilic and hydrophilic portions. The structure of the lipid bilayer is similar to the membranes enveloping animal cells, and are a result of amphipathic lipids arranged such that the hydrophobic portions of the lipid orient toward the center of the bilayer while the hydrophilic headgroups orient towards the inner or outer aqueous phases.

Liposome formulations for pharmaceutical applications can be made either by combining drug and lipid before formation of the vesicles, or by "loading" lipid vesicles with drug after they are formed. Upon administration to a patient, liposomes biodistribute and interact with cells in the body according to route of administration, vesicular composition, and vesicular size. Charge, chemistry, and the inclusion on the vesicle surface of protective polymers or targeting moieties, all change the way liposomes behave in the patient.

Despite the earlier pioneering research in developing liposome formulations for pharmaceutical use, the further development of liposomes to administer pharmaceuticals has presented problems with regard to both drug encapsulation in the manufacturing process and drug release from the vesicle during therapy.

For drug encapsulation, there is a need to increase the trapping efficiency such that the drug to lipid ratio is as high as possible, while maintaining the original chemical integrity of both drug and lipid. Consequently, the drug loading process should be mild and not subject the lipids, liposomes or drugs to harsh conditions such as extreme pH, high temperatures, or both. Once administration to a patient has occurred, drug release is a factor. Rapid release of pharmaceuticals from liposomes reduces the biodistribution benefits sought in utilizing lipid vesicle carriers. Accordingly, efforts to optimize pharmaceutical loading and to reduce the rate of release of pharmaceuticals from lipid vesicles have continued. For clinical applications, the liposome formulations should also be capable of existing stably in a formulated state or in a ready-to-mix kit to allow for shipping and storage.

What is needed in the art are new methods for the preparation of stable liposome formulations of therapeutic agents which are easy to prepare, provide suitable retention of the therapeutic agent, and which provide high drug to lipid ratios. Quite surprisingly, the present invention fulfills these and other needs.

SUMMARY OF THE INVENTION

The present invention provides methods for the preparation of stable liposome formulations of protonatable therapeutic agents. The method involves loading a therapeutic agent into preformed liposomes having a methylamine concentration gradient across the lipid bilayer of the liposomes. This method provides liposome formulations which are more stable, more cost effective, and easier to prepare in a clinical environment than those previously available. Additionally, these methods have application to a broader spectrum of pharmaceutical agents than methods previously described. The present invention also provides the pharmaceutical compositions prepared by the above method, a kit for the preparation of liposome formulations of therapeutic agents, and methods for their use.

Although not intending to be bound by any particular theory, it is postulated that neutral therapeutic agents can be loaded into preformed liposomes having a methylamine concentration gradient across their lipid bilayer by a mechanism illustrated in FIG. 1. In this particular embodiment, liposomes are formed having an encapsulated medium which contains a methylammonium salt. The external medium which originally has the composition of the encapsulated medium is exchanged with a neutral external medium. A therapeutic agent such as doxorubicin or ciprofloxacin (structures shown in FIG. 2) which is both lipophilic and which can be protonated is drawn toward the liposomes' encapsulated medium by both its polarity and the methylammonium ion gradient which is established across the bilayer. Methylamine diffuses out of the liposomes as the therapeutic agents are drawn in and protonated, thereby maintaining the differential (see FIG. 1).

The liposomes of this invention may be prepared with therapeutic agents which precipitate at pH ranges usual in the preparation and loading of lipid vesicles by conventional means. Further advantages for these liposomal compositions include a long shelf life which is a result of the lipids not being exposed to harsh conditions which can hydrolyze them.

The present invention also provides a method for reducing the rate of release of a protonatable therapeutic agent from lipid vesicles. In this method, a transmembrane potential, oriented to retain the agent in the lipid vesicles, is generated across the lipid vesicle membranes. As described in detail below, it has been surprisingly found that such a methylamine gradient is capable of producing over a thousand-fold reduction in the rate of release of protonatable therapeutic agents such as ciprofloxacin and doxorubicin from liposomes. Additionally, the method can be used with essentially any protonatable material which can be encapsulated in a lipid vesicle. The methylamine gradient can be generated after encapsulation of the protonatable compound or can be the result of lipid vesicle formation.

In addition to the foregoing methods, the invention also provides the products produced by practicing the methods, namely pharmaceutical preparations comprising a pharmaceutical agent which has been loaded into lipid vesicles by means of a methylamine gradient.

The present invention provides fast, safe, stable, efficient and inexpensive methods for loading amphipathic therapeutic agents into liposomes. The resulting compositions release the therapeutic agent slowly in the patient and therefore achieve maximal efficacy in vivo. The bitter taste and smell of pharmaceuticals such as ciprofloxacin can be masked using the invention, and it can be used to load drugs that are hydrochloride salts and therefore have a low solution pH. As a result, the present invention can be used to prepare pharmaceutical compositions that can not be generated in large quantities by any other technique.

DETAILED DESCRIPTION OF THE INVENTION

CONTENTS

Figure 1:
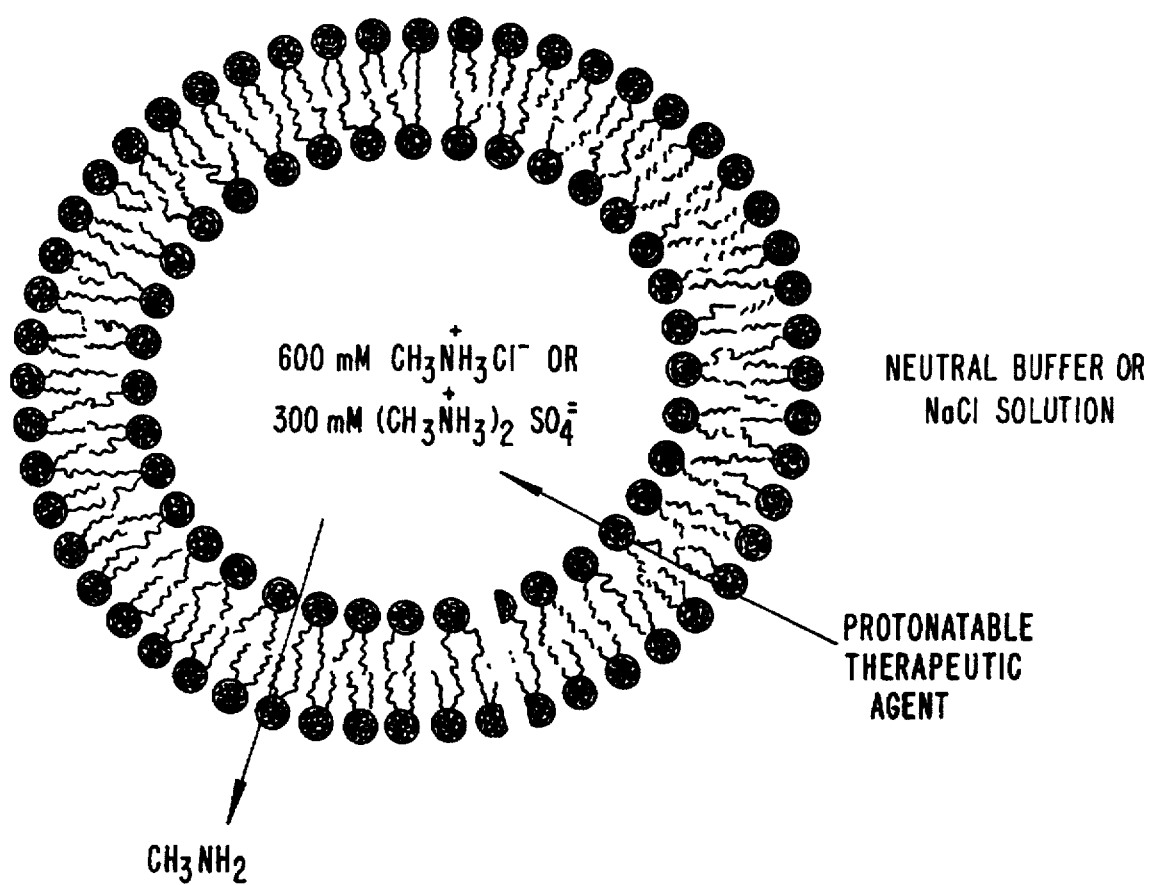
FIG. 1 shows a model of a liposome used to load a protonatable therapeutic agent.
Figure 2:
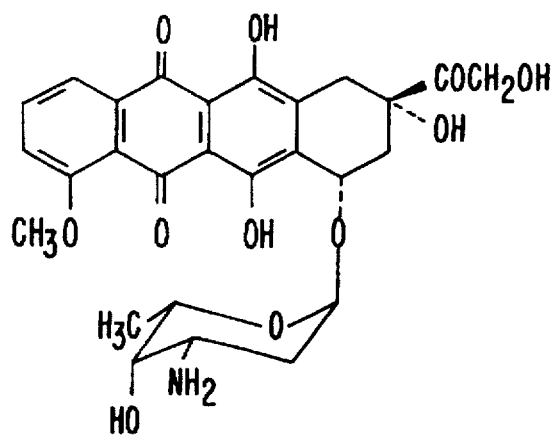
FIG. 2 shows the structures of doxorubicin and ciprofloxacin, two therapeutic agents which can be loaded and retained in liposomes according to the present invention.
Figure 2:
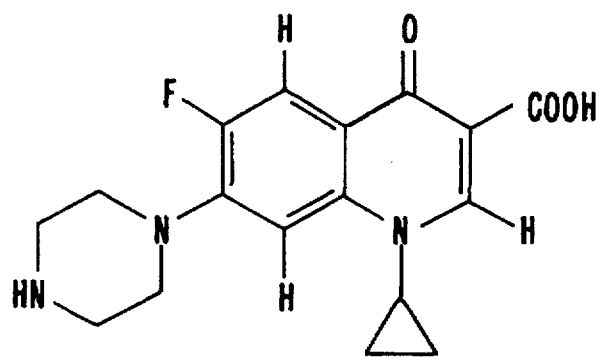

I. Glossary
II. General
III. Methods of Loading Therapeutic Agents Into Liposomes
IV. Methods of Retaining Therapeutic Agents In Liposomes
V. Pharmaceutical Formulations
VI. Administration of Liposome Formulations
VII. Examples
VIII. Conclusion I. Glossary The following abbreviations are used herein: DOX, doxorubicin; Cer, ceramide; Chol, cholesterol; CIP, ciprofloxacin; DPPC, dipalmitoyl phosphatidylcholine; DSPC, distearoyl phosphatidylcholine; DTT, dithiothreitol; EDAS, ethylenediammonium sulfate; HBS, Hepes buffered saline; LUV, large unilamellar vesicles; MAC, methylammonium chloride; MAS, methylammonium sulfate; MLV, multilamellar vesicles; MPB, 4-(maleimidophenyl)butyryl; PE, phosphatidylethanolamine; PEG, polyethylene glycol; PEG-Cer-$C_{20}$, 1-O-(2'-(ω-methoxypolyethyleneglycol)succinoyl)-2-N-arachidoyl-sphingosine; PEG-Cer-$C_{14}$, 1-O-(2'-(ω-methoxypolyethyleneglycol)succinoyl)-2-N-myristoyl-sphingosine; POPC, palmitoyloleoylphosphatidylcholine; and Sph, sphingomyelin.

As used herein, the terms "pharmaceutical preparation" and "protonatable agent," have the following meanings: pharmaceutical preparation means a composition of matter suitable for administration to humans or animals and comprising a biologically active material and appropriate buffers, diluents, carriers, and the like; and protonatable agent means an agent which can exist in a charged state when dissolved in an aqueous medium. Examples of protonatable agents include compounds having an amino group which can be protonated in acidic media, and compounds which are zwitterionic in neutral media (i.e., amino acids and agents such as ciprofloxacin) and which can also be protonated in acidic environments.

The term "lipid" refers to any suitable material resulting in a bilayer such that a hydrophobic portion of the lipid material orients toward the bilayer while a hydrophilic portion orients toward the aqueous phase. Amphipathic lipids are necessary as the primary lipid vesicle structural element. Hydrophilic characteristics derive from the presence of phosphato, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group(s). The preferred amphipathic compounds are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphasphatidylcholine or dilinoleoylphosphatidylcholine could be used. Other compounds lacking in phosphorus, such as sphingolipid and glycosphingolipid families are also within the group designated as lipid. Additionally, the ampipathic lipids described above may be mixed with other lipids including triglycerides and sterols.

As used herein, the term "tissue" refers to any pathological cell or group of cells that exhibit a similar pathological trait. For example, the trait may be malignant transformation. Alternatively, the trait may be intracellular infection. Generally, the tissue will include cells that originate from the same cell type.

II. General

The liposomes which are used in the present invention are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream.

Typically, the major lipid component in the liposomes is phosphatidylcholine. Phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Phosphatidylcholines containing saturated fatty acids with carbon chain lengths in the range of $C_{14}$ to $C_{22}$ are preferred. Phosphatidylcholines with mono or diunsaturated fatty acids and mixtures of saturated and unsaturated fatty acids may also be used. Other suitable lipids include phosphonolipids in which the fatty acids are linked to glycerol via ether linkages rather than ester linkages. Liposomes useful in the present invention may also be composed of sphingomyelin or phospholipids with head groups other than choline, such as ethanolamine, serine, glycerol and inositol. Preferred liposomes will include a sterol, preferably cholesterol, at molar ratios of from 0.1 to 1.0 (cholesterol:phospholipid). Most preferred liposome compositions are distearoylphosphatidylcholine/cholesterol, dipalmitoylphosphatidylcholine/cholesterol, and sphingomyelin/cholesterol. Methods used in sizing and filter-sterilizing liposomes are discussed below.

The liposomes can be prepared by any of the techniques now known or subsequently developed for preparing liposomes. For example, the liposomes can be formed by the conventional technique for preparing multilamellar lipid vesicles (MLVs), that is, by depositing one or more selected lipids on the inside walls of a suitable vessel by dissolving the lipids in chloroform and then evaporating the chloroform, and by then adding the aqueous solution which is to be encapsulated to the vessel, allowing the aqueous solution to hydrate the lipid, and swirling or vortexing the resulting lipid suspension. This process engenders a mixture including the desired liposomes.

Alternatively, techniques used for producing large unilamellar lipid vesicles (LUVs), such as reverse-phase evaporation, infusion procedures, and detergent dilution, can be used to produce the liposomes. A review of these and other methods for producing lipid vesicles can be found in the text Liposome Technology, Volume I, Gregory Gregoriadis Ed., CRC Press, Boca Raton, Fla., (1984), which is incorporated herein by reference. For example, the lipid-containing particles can be in the form of steroidal lipid vesicles, stable plurilamellar lipid vesicles (SPLVs), monophasic vesicles (MPVs), or lipid matrix carriers (LMCs) of the types disclosed in Lenk, et al. U.S. Pat. No. 4,522,803, and Fountain, et al. U.S. Pat. Nos. 4,588,578 and 4,610,868, the disclosures of which are incorporated herein by reference. A particularly preferred method for preparing LUVs is described in U.S. Pat. No. 5,008,050.

Additionally, in the case of MLVs, if desired, the liposomes can be subjected to multiple (five or more) freeze-thaw cycles to enhance their trapped volumes and trapping efficiencies and to provide a more uniform interlamellar distribution of solute (Mayer, et al., J. Biol. Chem. 260:802–808 (1985)).

Following liposome preparation, the liposomes may be sized to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposomes to a desired size.

One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size determination.

Extrusion of liposome through a small-pore polycarbonate membrane or an asymmetric ceramic membrane is also an effective method for reducing liposome sizes to a relatively well-defined size distribution (see, U.S. Pat. No.

5,008,050 and Hope, et al., in: Liposome Technology, vol. 1, 2d ed. (G. Gregoriadis, Ed.) CRC Press, pp. 123–139 (1992), the disclosures of which are incorporated herein by reference). Typically, the suspension is cycled through the membrane one or more times until the desired liposome size distribution is achieved. The liposomes may be extruded through successively smaller-pore membranes, to achieve a gradual reduction in liposome size. For use in the present inventions, liposomes having a size of from about 0.05 microns to about 0.15 microns are preferred. Other useful sizing methods such as sonication, solvent vaporization or reverse phase evaporation are known to those of skill in the art.

Liposomes prepared in the method of the invention may be dehydrated for longer storage. For this purpose, two basic approaches are provided. In one approach, the lipid vesicles are loaded with the therapeutic agent according to the method of the invention, dehydrated for purposes of storage, shipping, and the like, and then rehydrated at the time of use. Alternatively, the lipid vesicles may be formed without the protonatable therapeutic agent, dehydrated for storage, as above, and then at or near the time of use, rehydrated using a solution of the protonatable therapeutic agent such that the methylamine gradient is created, and the pharmaceutical agent is loaded.

In either case, the liposomes are preferably dehydrated under reduced pressure using standard freeze-drying equipment or equivalent apparatus. The lipid vesicles and their surrounding medium can also be frozen in liquid nitrogen before being dehydrated or not, and placed under reduced pressure. Dehydration without prior freezing takes longer than dehydration with prior freezing, but the overall process is gentler without the freezing step, and thus there is subsequently less damage to the lipid vesicles and a smaller loss of the internal contents. Dehydration without prior freezing at room temperature and at a reduced pressure provided by a vacuum pump capable of producing a pressure of about 1 mm Hg typically takes between approximately 24 and 36 hours, while dehydration with prior freezing under the same conditions generally takes between approximately 12 and 24 hours.

To ensure that the liposomes will survive the dehydration process without losing a substantial portion of their internal contents, it is important that one or more protective sugars be available to interact with the lipid vesicle membranes and keep them intact as the water in the system is removed. A variety of sugars can be used, including such sugars as trehalose, maltose, sucrose, glucose, lactose, and dextran. In general, disaccharide sugars have been found to work better than monosaccharide sugars, with the disaccharide sugars trehalose and sucrose being most effective. Other more complicated sugars can also be used. For example, aminoglycosides, including streptomycin and dihydrostreptomycin, have been found to protect lipid vesicles during dehydration.

Typically, one or more sugars are included as part of either the internal or external media of the lipid vesicles. Most preferably, the sugars are included in both the internal and external media so that they can interact with both the inside and outside surfaces of the liposomes' membranes. Inclusion in the internal medium is accomplished by adding the sugar or sugars to the buffer which becomes encapsulated in the lipid vesicles during the lipid vesicle formation process. Since in most cases this buffer also forms the bathing medium for the finished lipid vesicles, inclusion of the sugars in the buffer also makes them part of the external medium. Of course, if an external medium other than the original buffer is used, e.g., to create a transmembrane potential (see above), the new external medium should also include one or more of the protective sugars.

The amount of sugar to be used depends on the type of sugar used and the characteristics of the lipid vesicles to be protected. See, U.S. Pat. No. 4,880,635 and Harrigan, et al., Chem. Phys. Lipids 52:139–149 (1990), the disclosures of which are incorporated herein by reference. Persons skilled in the art can readily test various sugar types and concentrations to determine which combination works best for a particular lipid vesicle preparation. In general, sugar concentrations on the order of 100 mM and above have been found necessary to achieve the highest levels of protection. In terms of moles of membrane phospholipid, millimolar levels on the order of 100 mM correspond to approximately 5 moles of sugar per mole of phospholipid.

In the case of dehydration without prior freezing, if the lipid vesicles being dehydrated are of the type which have multiple lipid layers and if the dehydration is carried to an end point where between about 2% and about 5% of the original water in the preparation is left in the preparation, the use of one or more protective sugars may be omitted.

Once the lipid vesicles have been dehydrated, they can be stored for extended periods of time until they are to be used. The appropriate temperature for storage will depend on the make up of the lipid vesicles and the temperature sensitivity of whatever materials have been encapsulated in the lipid vesicles. For example, as is known in the art, various pharmaceutical agents are heat labile, and thus dehydrated lipid vesicles containing such agents should be stored under refrigerated conditions so that the potency of the agent is not lost. Also, for such agents, the dehydration process is preferably carried out at reduced temperatures, rather than at room temperature.

In certain embodiments, it is desirable to target the liposomes of the invention using targeting moieties that are specific to a particular cell type, tissue, and the like. Targeting of liposomes using a variety of targeting moieties (e.g., ligands, receptors and monoclonal antibodies) has been previously described (see, e.g., U.S. Pat. Nos. 4,957,773 and 4,603,044, both of which are incorporated herein by reference).

Examples of targeting moieties include monoclonal antibodies specific to antigens associated with neoplasms, such as prostate cancer specific antigen. Tumors can also be diagnosed by detecting gene products resulting from the activation or overexpression of oncogenes, such as ras or c-erB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (IBVc, HBVs) hepatitis C antigens, Epstein-Barr virus antigens, human immunodeficiency type-I virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see, Renneisen, et al., J. Biol. Chem., 265:16337–16342 (1990) and Leonetti, et al., Proc. Natl. Acad. Sci. (USA) 87:2448–2451 (1990), both of which are incorporated herein by reference).

Targeting mechanisms generally require that the targeting agents be positioned on the surface of the liposome in such a manner that the target moieties are available for interaction with the target, for example, a cell surface receptor. The liposome is typically fashioned in such a way that a connector portion is first incorporated into the membrane at the time of forming the membrane. The connector portion must have a lipophilic portion which is firmly embedded and anchored in the membrane. It must also have a hydrophilic portion which is chemically available on the aqueous surface of the liposome. The hydrophilic portion is selected so that it will be chemically suitable to form a stable chemical bond with the targeting agent which is added later. Therefore, the connector molecule must have both a lipophilic anchor and a hydrophilic reactive group suitable for reacting with the target agent and holding the target agent in its correct position, extended out from the liposome's surface. In some cases it is possible to attach the target agent to the connector molecule directly, but in most instances it is more suitable to use a third molecule to act as a chemical bridge, thus linking the connector molecule which is in the membrane with the target agent which is extended, three dimensionally, off of the vesicle surface.

III. Methods of Loading Therapeutic Agents Into Liposomes

Traditional methods of loading conventional drugs into liposomes include an encapsulation technique and a transmembrane potential loading method. In the encapsulation technique, the drug and liposome components are dissolved in an organic solvent or mixture of solvents in which all species are miscible, and then concentrated to a dry film. A buffer is then added to the dried film and liposomes are formed having the drug incorporated into the vesicle walls. In a modification of this encapsulation technique, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers.

Encapsulation methods, often referred to a "passive loading" suffer from several limitations. One such limitation is the low drug-to-lipid (D/L) ratio which is achieved. With low D/L ratios, larger amounts of lipids must be administered in order to provide a suitable drug concentration in vivo. Related to this low D/L ratio is the inefficiency of drug uptake into the liposomes which can result in substantial waste of the expensive pharmaceutical agents. Alternatively, recycling and reisolation of the unencapsulated pharmaceutical agents results in additional costs for preparation.

Alternative loading processes, termed "active loading," involve the use of transmembrane potentials. Transmembrane potential loading has been described in detail in U.S. Pat. No. 4,885,172, U.S. Pat. No. 5,059,421, U.S. Pat. No. 5,171,578, U.S. Pat. No. 5,316,771 and U.S. Pat. No. 5,380,531. Briefly, the transmembrane potential loading method is used for a number of conventional drugs which can exist in a charged state when dissolved in an appropriate aqueous medium. Preferably, the drug will be relatively lipophilic so that it will partition into the liposome membranes. The loading process is carried out by creating a transmembrane potential across the bilayers of the liposomes. The transmembrane potential is generated by creating a concentration gradient for one or more charged species (e.g., $Na^+$, $K^+$, $H^+$ and/or $NH_4^+$) across the membranes. This concentration gradient is generated by producing liposomes having different internal and external media. Thus, for a drug which is negatively charged when ionized, a transmembrane potential is created across the membranes which has an inside potential which is positive relative to the outside potential. For a drug which is positively charged, the opposite transmembrane potential would be used.

Despite this more "active" loading process, some of these methods still suffer from inefficient drug loading or limitations resulting from the particular media used. For example, Mayer, et al., J. Biol. Chem. 260:802–808 (1985), describe the loading of a local anesthetic dicubaine, into liposomes using Na+ and K+ gradients. However, only 52% loading was achieved. Methods which involve H+ ion gradients (or pH gradients) have proven useful for a number of liposome loading applications. Nevertheless, these methods also have their limitations. For example, one method which uses a pH gradient involves preparing liposomes having an acidic interior medium and a neutral exterior medium. The use of an unphysiologically acidic pH can degrade some drugs and also promote lipid hydrolysis and subsequent leakage of any encapsulated drug. Additionally, the method does not appear to be useful for those drugs which have both a basic amine functionality and a carboxylic acid functionality (e.g., amino acids, small peptides and zwitterionic drugs). For example, Chakrabarti, et al. U.S. Pat. No. 5,380,531 describes pH loading methods for amino acids and peptides in which the amino acids and peptides are first derivatized to their ester or amide forms. Chakrabarti, et al. also note that the method does not work for the more basic amino acid esters and peptide esters such as histidine methyl ester, $(Lys)_5$ methyl ester and $Lys-(Ala)_4$ methyl ester. Other problems which exist for pH loading methods involve the limited solubility of some drugs in a neutral external medium. For example, the quinolone antibacterial agent ciprofloxacin is essentially insoluble in water in the pH range 6 to 8. If the external pH is lowered to about 5 (a point at which ciprofloxacin is adequately soluble) the gradient is insufficient for rapidly and efficiently loading the drug.

More recently, Barenholz, et al. U.S. Pat. Nos. 5,316,771 and 5,192,549 have described an active loading method which utilizes a $NH_4^+$ ion gradient.

Barenholz, et al. note that liposome loading using a $NH_4^+$ ion gradient is useful for weak amphipathic compounds having either weak basic or acidic moieties. Additionally, Barenholz, et al. note that within a group of weak bases, the more hydrophobic of the group will load more readily. While this method provides an alternative strategy for loading of certain compounds, there still exists a need in the art for methods of broader application, for example, methods which are suitable for compounds which possess both basic and acidic functionality and which are relatively insoluble in water at neutral pH.

Surprisingly, we have found that the use of methylammonium ion gradients enable the rapid loading and retention of drugs such as ciprofloxacin into liposomes.

Moreover, methods which use methylammonium ion gradients provide a broader range of loading possibilities than are available with gradients using other amines such as ethanolamine or glucosamine.

Accordingly, the present invention provides in one aspect a method of preparing a stable liposome formulation of a protonatable therapeutic agent. In this method, liposomes are first prepared which encapsulate an aqueous solution of a methylammonium salt. Following preparation of the liposomes, a concentration gradient of methylamine across the liposome membranes is established, and the resulting liposome mixture is incubated with a neutral form of the protonatable therapeutic agent. The therapeutic agent is drawn into the liposome as a result of the concentration gradient of methylamine, and once encapsulated, is protonated and trapped.

Liposomes which encapsulate an aqueous solution of a methylamine salt can be prepared by any of the methods described above. Subsequent loading of the protonatable therapeutic agent into the liposomes will be dependent on the methylamine concentration gradient (or methylammonium ion gradient) and the pH gradient which also results from a change in methylamine concentrations between the lipid bilayers. The gradients are created by forming liposomes in a methylammonium salt solution, followed by removal or dilution of the salt from the external aqueous phase of the liposomes. A number of methylammonium salts are useful in the present invention, including methylammonium chloride, methylammonium sulfate, methylammonium citrate and methylammonium acetate. Other salts which are suitable in pharmaceutical formulations are known to those of skill in the art. The concentration of the methylammonium salt solution which is encapsulated can vary from about 50 mM to about 1M, however concentrations of 200 mM to 800 mM are preferred, with 300 mM to 600 mM being particularly preferred. In general an initial methylammonium ion concentration of about 600 mM is the most preferred. To create the concentration gradient, the original external medium is replaced by a new external medium having a different concentration of the charged species or a totally different charged species. The replacement of the external medium can be accomplished by various techniques, such as, by passing the lipid vesicle preparation through a gel filtration column, e.g., a Sephadex column, which has been equilibrated with the new medium, or by centrifugation, dialysis, or related techniques.

Depending upon the permeability of the lipid vesicle membranes, the full transmembrane potential corresponding to the concentration gradient will either form spontaneously or a permeability enhancing agent, e.g., a proton ionophore may have to be added to the bathing medium. If desired, the permeability enhancing agent can be removed from the preparation after loading has been completed using chromatography or other techniques. In either case, a transmembrane potential having a magnitude defined by the Nernst equation will appear across the lipid vesicles' membranes. The change in composition of the external phase causes an outflow of neutral methylamine from the interior encapsulated medium to the external medium. This outflow also results in a reverse pH gradient by accumulation of hydrogen ions left behind in the internal aqueous phase. An influx of a neutral form of a protonatable therapeutic agent into the liposomes replaces the methylamine.

In accordance with the invention, it has also been found that the methylamine gradient can be used to load protonatable therapeutic agents into the lipid vesicles regardless of the pH of the external solution. This is very surprising in light of earlier loading methods. Still further, once lipid vesicles having a concentration gradient and thus a methylamine gradient of the appropriate orientation have been prepared, the process of loading pharmaceutical agents into the lipid vesicles reduces to the very simple step of adding the agent to the external medium. Once added, the methylamine gradient will automatically load the agent into the lipid vesicles. As described in detail in the Examples below, the loading is not only simple, but is also extremely efficient. As also described in the Examples below, it has been found that trapping efficiencies for pharmaceutical agents of 90% and higher can be readily achieved with the methylamine/methylammonium ion gradient loading technique.

The methylamine gradient loading method can be used with essentially any therapeutic agent which can exist in a charged state when dissolved in an appropriate aqueous medium (e.g., organic compounds which include an amino group which can be protonated and some zwitterionic compounds such as the quinolone antibacterial agents).

Preferably, the agent, or drug, should be relatively lipophilic so that it will partition into the lipid vesicle membranes. Examples of some of the pharmaceutical agents which can be loaded into lipid vesicles by this method include doxorubicin, mitomycin, bleomycin, daunorubicin, streptozocin, vinblastine, vincristine, mechlorethamine hydrochloride, melphalan, cyclophosphamide, triethylenethiophosphoramide, carmustine, lomustine, semustine, fluorouracil, hydroxyurea, thioguanine, cytarabine, floxuridine, decarbazine, procarbazine, and ciprofloxacin. Preferably, the drugs which are loaded into liposomes using the present methods will be anthraquinone drugs selected from the group consisting of doxorubicin, daunomycin, carcinomycin, N-acetyladriamycin, N-acetyldaunomycin, rubidazone, 5-imidodaunomycin, musettamycin, rudolfomycin, aclacinomycin, marcellomycin, descarbomethoxymarcellomycin, descarbomethoxyrudolfomycin, and mitoxanthrone; vincristine and its analogs; cis-platinum; and the quinolone antibacterial agents.

The present method has proven especially suitable for loading drugs such as ciprofloxacin. As noted above, ciprofloxacin is an antibacterial agent which is zwitterionic in the pH range of about 3.5 to about 11.5. Additionally, ciprofloxacin has limited solubility in water at neutral in the pH range of about 5.5 to about 9.5. When added to water, ciprofloxacin produces an aqueous mixture having a pH of about 3.5 to 4.0. Any attempts to buffer this ciprofloxacin solution or adjust the pH result in the precipitation of the drug. Despite these problematic characteristics, the present method can be applied to liposome loading of ciprofloxacin and related quinolone antibacterial agents such as norfloxacin, ofloxacin and enoxacin (see, Pernandes, et al., ANNUAL REPORTS IN MEDICINAL CHEMISTRY Vol. 23, Academic Press, San Diego, Calif., Chapter 14, pp. 133–140 (1988), incorporated herein by reference).

In addition to loading a single therapeutic agent, the method can be used to load multiple therapeutic agents, either simultaneously or sequentially. Also, the lipid vesicles into which the protonatable therapeutic agents are loaded can themselves be pre-loaded with other pharmaceutical agents or other drugs using conventional encapsulation techniques (e.g., by incorporating the drug in the buffer from which the lipid vesicles are made). Since the conventionally loaded materials need not be protonatable, this approach provides great flexibility in preparing lipid vesicle-encapsulated "drug cocktails" for use in cancer therapies. Indeed, essentially all types of anti-cancer drugs can be pre-loaded, at least to some extent, in either the lipid or aqueous portion of the lipid vesicles. Of course, if desired, one or more of the protonatable drugs listed above can be pre-loaded and then the same or a different drug added to the lipid vesicles using the transmembrane potential approach.

The liposome formulations of therapeutic agents may be dehydrated for extended storage, and rehydrated just prior to use. Techniques for freeze-drying are described in the General section above.

IV. Methods of Retaining Therapeutic Agents in Liposomes

Turning now to the aspects of the invention relating to reducing the rate of release of an protonatable pharmaceutical agent from lipid vesicles, it has been surprisingly found that the rate of release can be markedly reduced by creating a transmembrane potential across the lipid vesicle membranes which is oriented to retain the agent in the lipid vesicles.

If the lipid vesicles have been loaded by means of a transmembrane potential produced by such a concentration gradient, simply keeping the lipid vesicles in an external medium which will maintain the original concentration gradient will produce the desired reduction in the rate of release. Alternatively, if a methylamine gradient has not already been created across the lipid vesicle membranes, e.g., if the lipid vesicles have been loaded using a conventional technique, the desired methylamine gradient can be readily created by changing the composition of the external medium using the exchange techniques described above.

The reduced rate of release aspect of the invention can be used with essentially any protonatable biologically-active agent which can be encapsulated in a lipid vesicle. In particular, the technique can be used with the protonatable pharmaceutical agents listed above and with a variety of other protonatable drugs, including such drugs as local anesthetics, e.g., dibucaine and chlorpromazine; beta-adrenergic blockers, e.g., propranolol, timolol and labetolol; antihypertensive agents, e.g., clonidine, and hydralazine; anti-depressants, e.g., imipramine, amitriptyline and doxepim; anti-convulsants, e.g., phenytoin; anti-emetics, e.g., procainamide and prochlorperazine: antihistamines. e.g., diphenhydramine, chlorpheniramine and promethazine; anti-arrhythmic agents, e.g., quinidine and disopyramide; anti-malarial agents, e.g., chloroquine; antibiotics, e.g. ciprofloxacin; and analgesics e.g., cocaine. In general, as the drug accumulates in the lipid vesicles, internal pH rises which will precipitate some drugs, making them less likely to leak out of the lipid vesicle.

V. Pharmaceutical Formulations

Pharmaceutical compositions comprising the liposomes of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of liposomes, in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, liposomes composed of irritating lipids may be diluted to low concentrations to lessen inflammation at the site of administration. For diagnosis, the amount of liposomes administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, it is often desirable to include polyethylene glycol- (PEG) or ganglioside $G_{M1}$-modified lipids to the liposomes. Addition of such components prevent liposome aggregation during coupling of the anti-ligand to the liposome. This also provides a means for increasing circulation lifetime and increasing the delivery of liposomes to the target tissues. Typically, the concentration of the PEG- or $G_{M1}$-modified lipids in the liposome membrane will be about 1–5%.

Liposome charge is an important determinant in liposome clearance from the blood, with negatively charged liposomes being taken up more rapidly by the reticuloendothelial system (Juliano, Biochem. Biophys. Res. Commun. 63:651 (1975)) and thus having shorter half-lives in the bloodstream. Liposomes with prolonged circulation half-lives are typically desirable for therapeutic and diagnostic uses (see, U.S. Application Ser. No. 08/316,429). For instance, liposomes which can be maintained from 8, 12, or up to 24 hours in the bloodstream are particularly preferred.

In another example of their use, lipid vesicle formulations may be incorporated into a broad range of topical dosage forms including but not limited to gels, oils, emulsions and the like. For instance, the suspension containing the lipid vesicle formulation may be added to the aqueous phase as an ingredient in the lipid vesicle preparation, and as such may be administered as topical creams, pastes, ointments, gels, lotions and the like for direct application.

The present invention also provides liposomes and protonatable therapeutic agents in kit form. The kit will typically be comprised of a container which is compartmentalized for holding the various elements of the kit. The therapeutic agents which are used in the kit are those agents which have been described above. In one embodiment, one compartment will contain a second kit for loading a protonatable therapeutic agent into a liposome just prior to use. Thus, the first compartment will contain a suitable agent in a neutral buffer which is used to provide an external medium for the liposomes, typically in dehydrated form in a first compartment. The liposomes are vesicles which have an encapsulated methylammonium salt. In other embodiments, the kit will contain the compositions of the present inventions, preferably in dehydrated form, with instructions for their rehydration and administration. In still other embodiments, the liposomes and/or compositions comprising liposomes will have a targeting moiety attached to the surface of the liposome. As noted in sections above, one striking advantage for the kits described is their broader applicability for the uptake and retention of drugs such as, for example, ciprofloxacin.

VI. Administration of Liposome Formulations

Once the therapeutic agent has been "loaded" into the liposomes, the combination can be administered to a patient by a variety of techniques.

Preferably, the pharmaceutical compositions are administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578. Particular formulations which are suitable for this use are found in Remington's Pharmaceutical Sciences, Mack Publishing Company, Philadelphia, PA, 17th ed. (1985). Typically, the formulations will comprise a solution of the liposomes suspended in an acceptable carrier, preferably an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Dosage for the liposome formulations will depend on the ratio of drug to lipid and the administrating physician's opinion based on age, weight, and condition of the patient.

The methods of the present invention may be practiced in a variety of hosts. Preferred hosts include mammalian species, such as humans, non-human primates, dogs, cats, cattle, horses, sheep, and the like.

In other methods, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The compositions of the present invention which further comprise a targeting antibody on the surface of the liposome are particularly useful for the treatment of certain malignant diseases, such as ovarian adenocarcinoma that has metastasized throughout the peritoneal cavity and metastatic lesions to the subarachnoid space that commonly adhere to the arachnoid or pia mater and threaten compression of the spinal cord. Adenocarcinoma of the breast commonly exhibits such a metastatic pattern.

The following examples are offered solely for the purposes of illustration, and are intended neither to limit nor to define the invention.

EXAMPLES

In the examples below, Example 1 illustrates difficulties associated with liposome uptake of ciprofloxacin using pH gradient methods. Example 2 illustrates differences in drug loading using a substituted ammonium ion gradient for the uptake of doxorubicin, vincristine and ciprofloxacin. Example 3 illustrates the use of a diamine for establishing ion gradients to facilitate drug uptake and the differences observed with different drugs. Example 4 illustrates the use of methylammonium sulfate to load a zwitterionic drug (ciprofloxacin) into liposomes. Example 5 illustrates attempts to load tryptophan (zwitterionic) into liposomes using methylammonium sulfate. Example 6 provides additional results for the loading of drugs into liposomes using methylammonium ion gradients and also shows the effect of vesicle composition, counterion, drug-to-lipid ratios and liposome surface conjugates. Examples 7 and 8 illustrate the retention of drugs in liposomes which were loaded using a methylammonium ion gradient.

Materials

Distearoyl phosphatidylcholine (DSPC) and dipalmitoyl phosphatidylcholine were obtained from Avanti Polar Lipids (Alabaster, Alabama, USA) and N-succinimidyl 3-(2-pyridyldithio) propionic acid (SPDP) was from Molecular Probes (Eugene, Oregon, USA). Doxorubicin, epirubicin and vincristine were obtained from Pharmacia, Inc., Mississauga, Ontario, Canada. Cholesterol, dithiothreitol (DTT), N-2-hydroxyethylpiperazine-N-2-ethanesulfonic acid (HEPES), Sephadex G-50, sepharose CL-4B, tryptophan and all salts, except those for which preparative methods are provided, were obtained from Sigma Chemical Company, St. Louis, Mo., USA. Purified N-(4-(maleimidophenyl)butyryl) distearoyl phosphatidylethanolamine (MPB-DSPE) was purchased from Northern Lipids Inc., Vancouver, British Columbia, Canada. Ciprofloxacin was obtained from Bayer, Inc. Healthcare Division, Etobicoke, Ontario, Canada. $PEG_{2000}$-Cer-C20 and $PEG_{2000}$-Cer-C14 are described in co-pending U.S. patent application Ser. No. 08/316,429.

Methylamine (40% w/v in water) and methylammonium chloride ($CH_3NH_3Cl$ or MAC) were purchased from BDH. Methylammonium sulfate (($CH_3NH_3)_2SO_4$ or MAS) was prepared by carefully titrating methylamine (40% by weight/volume in water) with concentrated sulfuric acid until the solution was slightly basic (pH 7.9). Some of the water was removed using a Brinkmann Rotavapor-R rotovap. The remaining water was removed azeotropically with absolute ethanol (5–6 additions) using the rotovap. The resulting salt was washed with anhydrous ether and the solvent was removed by filtration. Residual solvent was removed by placing the methylammonium sulfate under high vacuum overnight.

Methods

Lipid Vesicles

Egg phosphatidylcholine was hydrated in an appropriate buffer or salt solution (for example 300 or 600 mM MAC) at 25° C., and subjected to five cycles of freeze-thawing (liquid nitrogen at about −195° C. followed by water at 30° C.).

Distearyl or dipalmitoylphosphatidylcholine/cholesterol (55:45 mol:mol) (DSPC or DPPC/chol) was first dissolved in t-butanol or 10% ethanol/cyclohexane, then lyophilized. The lipid mixture was then hydrated in an appropriate buffer or salt solution (e.g. 600 mM MAC or 300 mM MAS) and freeze-thawed in the same manner as the egg phosphatidylcholine lipid except the temperature of the water for thawing was increased to 45° C. (for DPPC/chol) and to 65° C. (for DSPC/chol).

Sphingomyelin/ceramide/cholesterol (1:1:1 mole ratio Sph/Cer/Chol) mixtures were prepared as for DPPC/cholesterol above except that the lipids were initially lyophilized from benzene: methanol (7:3 vol:vol).

LUVs were prepared from the hydrated lipids above by extrusion through either 0.1 micron or 0.2 micron polycarbonate filters (Costar or Poretics, Inc.) at 25° C. or 45° C. The LUVs were then passed down spin-columns prepared with Sephadex G-50 (Sigma) in 150 mM NaCl (saline).

Drug-to-Lipid Ratios (D/L)

Drug-to-lipid ratios were determined as follows:

Aliquots of loaded lipid vesicles were taken at fixed time intervals, ranging from minutes to 24 hours after the addition of drug (e.g., doxorubicin or ciprofloxacin) and spun at 2500 rpm for 3 minutes. Drug to lipid ratios were determined from the spin/column samples taken before and after lipid vesicles were loaded. Lipid concentrations were determined using phosphate assays, and drug (doxorubicin) concentrations by spectrophotometric assay based on the absorbance of the drug at 480 nm. For ciprofloxacin, the loaded vesicles were subjected to a Bligh and Dyer extraction procedure using 200 mM NaOH, and the upper (aqueous phase) was removed and assayed spectrophotometrically at 274 nm against an upper phase blank to determine the drug concentrations.

EXAMPLE 1

This example illustrates the attempts to efficiently load liposomes with ciprofloxacin using a pH gradient.

Liposomes were prepared from egg phosphatidylcholine as described above. Citrate buffer (300 mM, pH 4.0) was used as the hydration buffer thereby providing the internal medium. After sizing, the 200 nm LUVs were passed down spin-columns to provide liposomes having an external medium of 150 mM NaCl. Ciprofloxacin was added to the external medium to achieve a D/L of 2.0. However, this amount resulted in lowering the pH of the external medium to about 4. Accordingly, ciprofloxacin was loaded into the liposomes in an amount which provided only a D/L ratio of 0.18 (<10% loading). If the pH of the internal medium was lowered to about 2, loading of only about 13% was achieved. Thus, while it is possible to achieve some loading of ciprofloxacin using internal citrate buffers, the D/L ratios are very low and highly acidic conditions are required. Such conditions can lead to lipid hydrolysis and subsequent leakage of the loaded drug.

EXAMPLE 2

This example illustrates the use of an ethanolamine gradient (ethanolammonium chloride) to provide liposomes loaded with doxorubicin, vincristine or ciprofloxacin.

Large unilammelar vesicles (LUVs) were prepared from DPPC and cholesterol as described above by hydrating the lipid mixture in 600 mM ethanolamine hydrochloride. The resulting mixture was sized to produce LUVs of about 100 nm. The vesicles were passed down a spin-column to provide an external medium of 150 mM NaCl.

For doxorubicin, uptake was performed at 60° C. for 15 min with an initial D/L ratio of 0.25. After the initial uptake period, the sample was divided into two aliquots. One aliquot was incubated at 60° C. and the other aliquot was incubated at 37° C. Within 5 min, essentially 100% of the drug was encapsulated. If the temperature was maintained at 60° C., approximately half of the doxorubicin leaked out over a period of 2.5 hr. However, if the temperature was lowered to 37° C., following uptake, complete retention was observed over 2.5 hr, and also after 94 hr at 4° C. (see FIG. 3).

For vincristine, the experiments were performed in the same manner as described for doxorubicin. The uptake of vincristine was also excellent (see FIG. 4, using an initial D/L ratio of 0.3), however some leakage did occur.

Uptake of ciprofloxacin was performed at 45° C. and 60° C. for initial D/L ratios of 0.38 and 0.91, respectively. As FIG. 5 indicates, the maximum D/L ratio achieved was of the order of 0.20–0.25, indicating an uptake of only about 27–40%.

Figure 3:
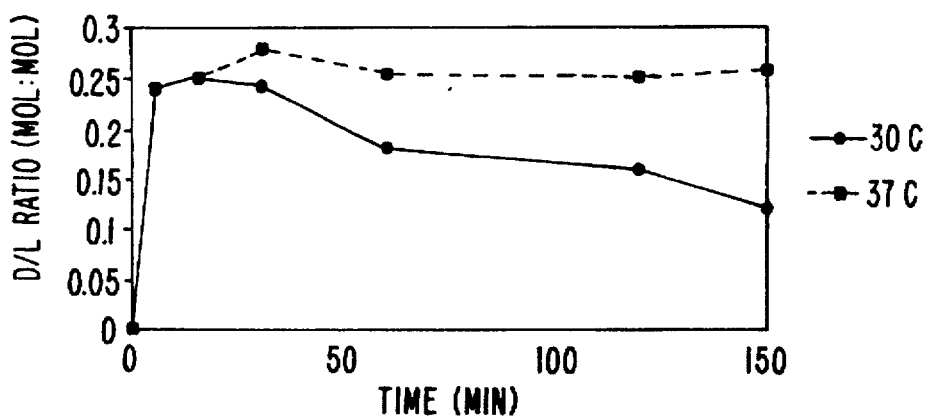
FIG. 3 shows the temperature dependent uptake and retention of doxorubicin in LUVs exhibiting 600 mM ethanolamine HCl gradients.
Figure 4:
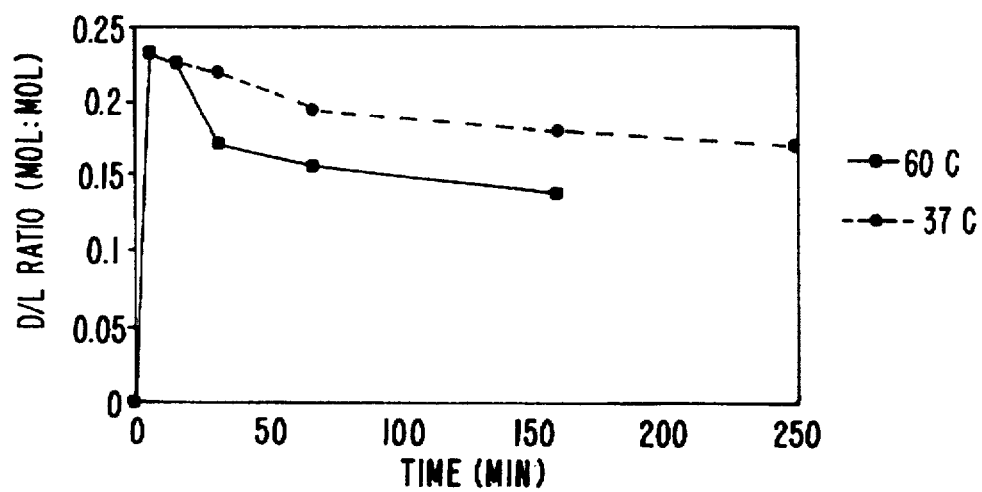
FIG. 4 shows the temperature dependent uptake and retention of vincristine in LUVs exhibiting ethanolamine HCl gradients.
Figure 5:
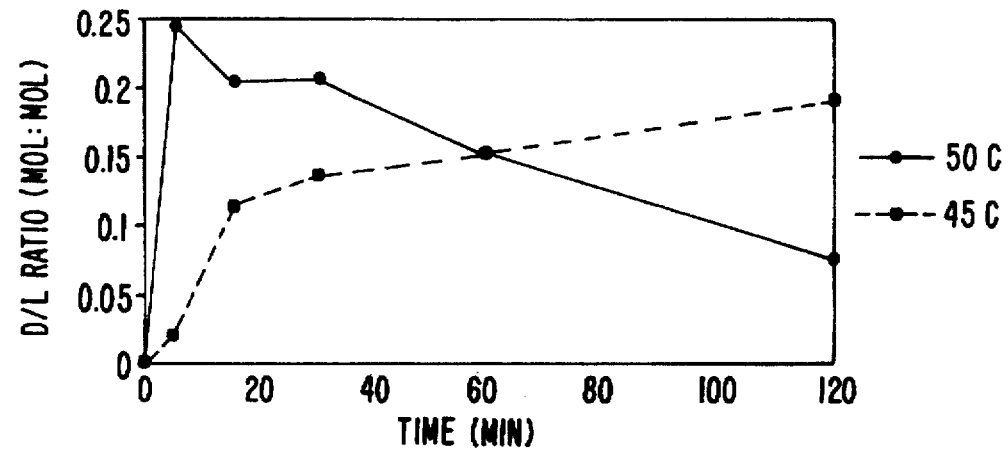
FIG. 5 shows the temperature dependent uptake and retention of ciprofloxacin in LUVs exhibiting 600 mM ethanolamine HCl gradients.

As FIGS. 3–5 indicate, ethanolammonium ion gradient loading can be useful for doxorubicin and vincristine under the appropriate conditions, but is not useful for the loading of ciprofloxacin.

EXAMPLE 3

This example illustrates the loading of lipid vesicles with doxorubicin, epirubicin, vincristine and ciprofloxacin using an ethylenediammonium sulfate ($^+H_4N$—$CH_2CH_2$—$NH_4^+$ $SO_4^{-2}$, EDAS) gradient.

Ethylenediammonium sulfate was prepared in a manner similar to that described above for methylammonium sulfate. LUVs (100 nm, DPPC/chol 55:45 containing 600 mM EDAS) were also prepared as described for ethanolammonium chloride vesicles. Following sizing, the LUVs were run through a spin-column to provide a 150 mM NaCl external medium.

Figure 6:
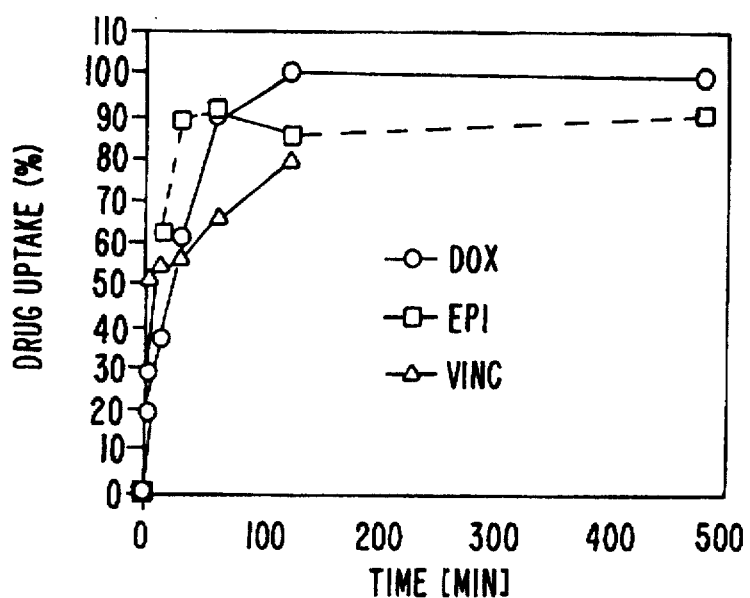
FIG. 6 shows the uptake and retention of doxorubicin, epirubicin, and vincristine in LUVs (DPPC/chol) exhibiting a 600 mM EDAS gradient at 60° C.

Uptake of doxorubicin, epirubicin and vincristine were all carried out at 60° C. As FIG. 6 demonstrates, uptake of doxorubicin and epirubicin was rapid (about 20 min) and provided over 90% encapsulation of the drugs. For vincristine, uptake was significantly slower, with only 80% uptake achieved in approximately 2 hours.

Figure 7:
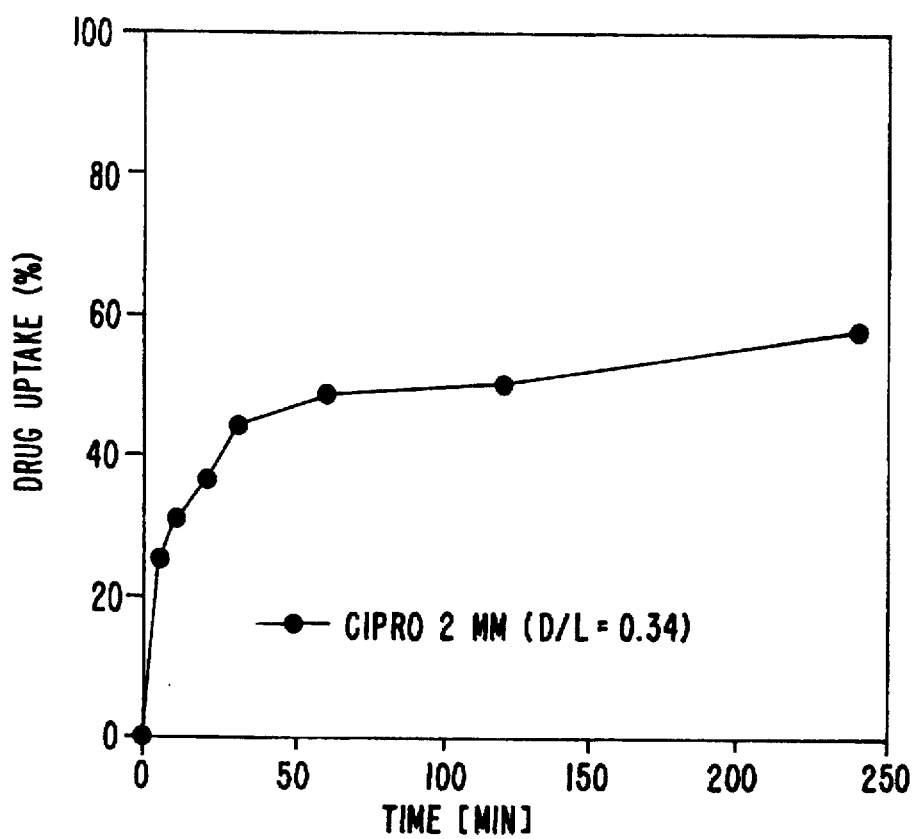
FIG. 7 shows the uptake of ciprofloxacin in POPC/chol LUVs exhibiting a 300 mM EDAS gradient with an external pH 5.5 citrate buffer.

The uptake of ciprofloxacin was significantly lower. Experiments with 200 nm LUVs and 300 mM EDAS as the internal medium resulted in less than 40% uptake over about 3 hours. A slight improvement in the percent uptake of ciprofloxacin was observed with EDAS if the external medium was buffered to about pH 5.5, using 25 mM citrate buffer. For 200 nm LUVs composed of POPC/chol containing 300 mM EDAS, the uptake at 60° C. was almost 60% (see FIG. 7).

Another diamino compound, lysine methyl ester hydrochloride, was also investigated for its ability to promote uptake of epirubicin. Only a 70% uptake was obtained after 1.3 hours at 60° C., providing an even lower efficiency than was obtained with EDAS.

As the above results indicate, EDAS is suitable for promoting the uptake of some drugs (e.g. doxorubicin and epirubicin) but is less suitable for others (vincristine) and quite inferior for promoting the uptake of drugs such as ciprofloxacin.

EXAMPLE 4

This example illustrates the use of a methylammonium sulfate ion gradient to promote liposome uptake of ciprofloxacin and provides a comparison with the method above which utilizes EDAS or a pH gradient.

Figure 8:
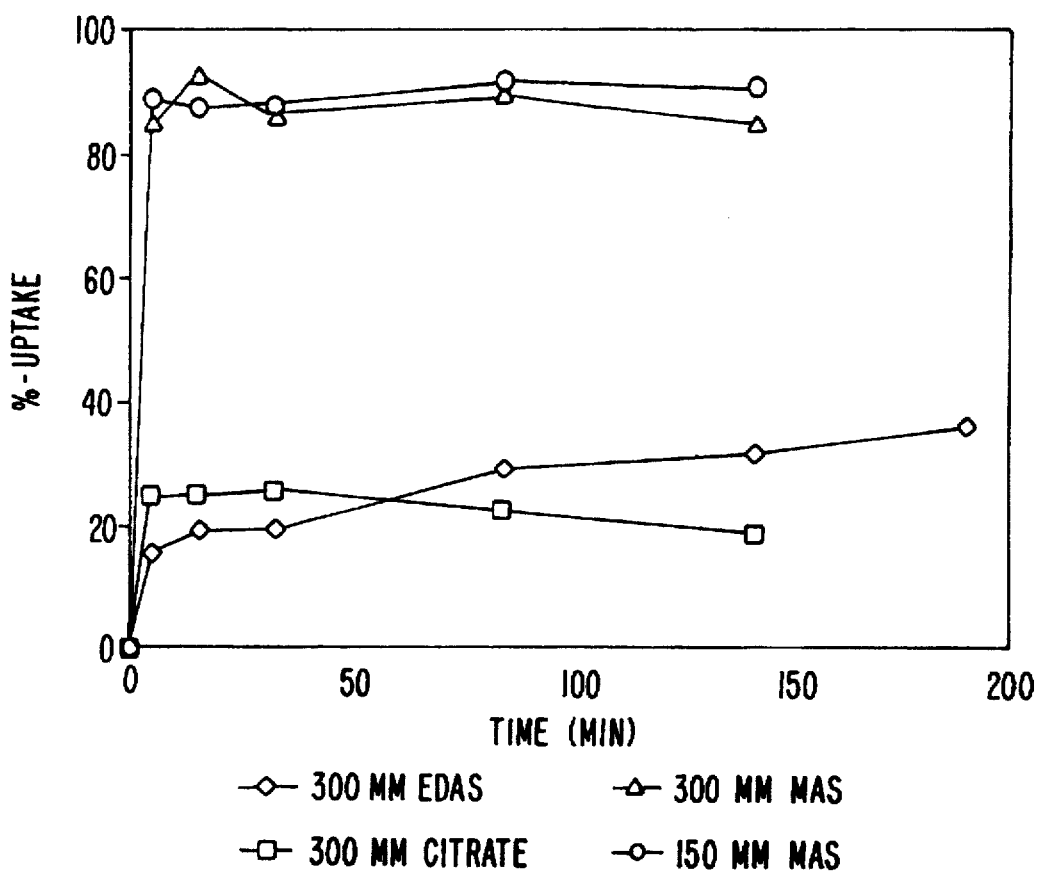
FIG. 8 shows the uptake of ciprofloxacin in DPPC/chol LUVs in response to amine gradients at 60° C.

LUVs (200 nm DPPC/chol) were prepared having the indicated internal medium (see FIG. 8) and an external medium of 150 mM NaCl. Encapsulation of ciprofloxacin was carried out at 60° C. for the time indicated, with an initial D/L ratio of 0.3. As FIG. 8 illustrates, both 150 mM methylammonium sulfate and 300 mM methylammonium sulfate provided about 90% encapsulation of ciprofloxacin within 10 minutes. If the vesicle interior contains 300 mM citrate (pH 4.0), only 25% uptake of ciprofloxacin is observed, and leakage begins after about 1 hour. Uptake using EDAS results in only a 40% uptake after about 3 hours.

Subsequent experiments investigated the ability of liposomes encapsulating methylammonium sulfate solutions to actively load other drugs. Excellent loading was found for ciprofloxacin, doxorubicin, epirubicin and vincristine.

EXAMPLE 5

This example illustrates the attempts to load tryptophan into liposomes.

Figure 9:
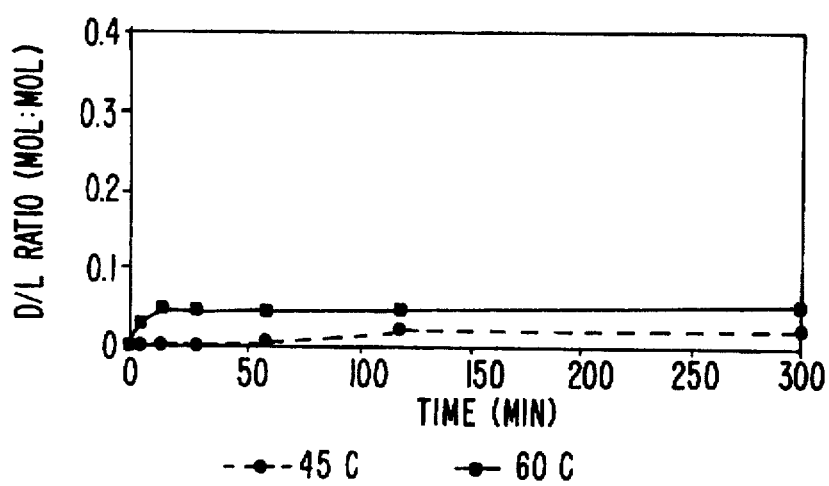
FIG. 9 shows the temperature dependent uptake of tryptophan in response to 300 mM methylammonium sulfate gradients.

As noted above, ciprofloxacin is zwitterionic at neutral pH and exhibits characteristics which make active loading into liposomes by such processes as pH gradients, very difficult. Surprisingly, ciprofloxacin has been found to be loaded into liposomes using a methylamine/methylammonium ion gradient (see Example 4). To see if this behavior extends to other common zwitterionic compounds, the temperature-dependent uptake of the amino acid tryptophan was investigated. The results are provided in FIG. 9. The initial tryptophan/lipid ratio was 1.0 using 100 nm LUVs composed of DPPC/Chol (55:45). As can be seen in FIG. 9, essentially no uptake was observed at 45° C. and very little (~5%) was observed at 60° C. Thus, the ability to encapsulate ciprofloxacin does not extend to zwitterions such as tryptophan.

EXAMPLE 6

This example provides further experiments to determine the effectiveness of methylamine/methylammonium salts at loading various drugs. Additionally, lipid vesicle composition, counterions and drug-to-lipid ratios were also investigated.

6.1 Vesicle composition

Figure 10A:
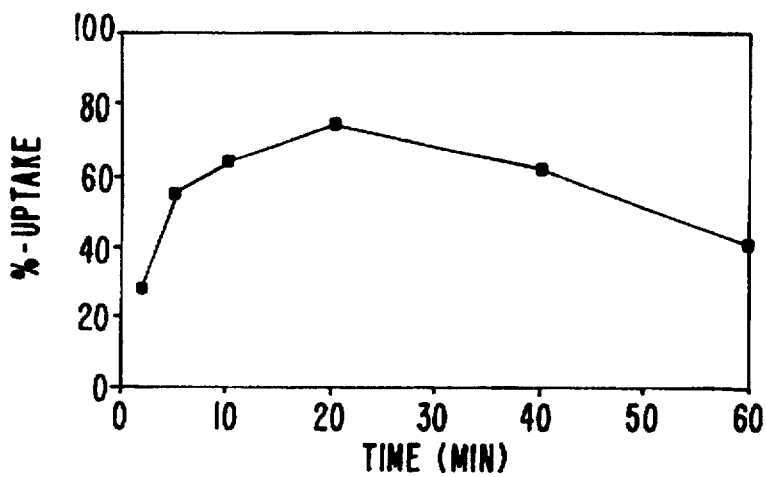
FIG. 10A shows the uptake of doxorubicin in 100 nm size unilamellar vesicles (LUVs) composed of egg phosphatidylcholine and formed in the presence of a gradient of 300 mM $CH_3NH_3Cl$ (methylammonium chloride or MAC), at a drug to lipid (molar) ratio of 0.26 and a temperature of 25° C.
Figure 10B:
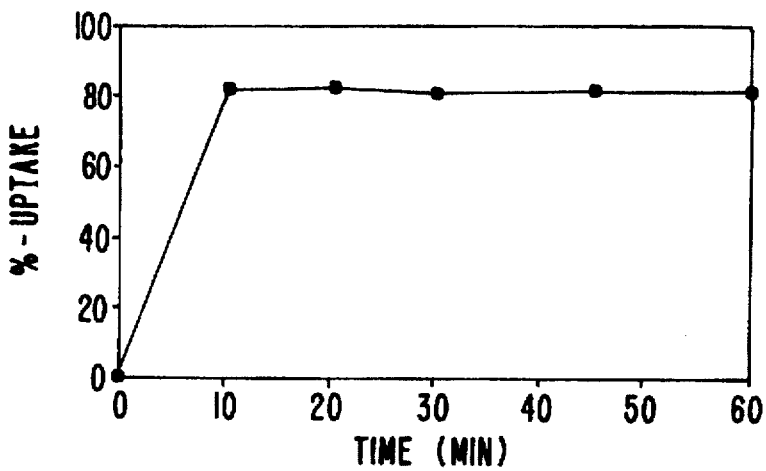
FIG. 10B show the improved retention of doxorubicin in egg phosphatidylcholine LUVs under the same conditions as in FIG. 10A except the liposomes were formed in MAC at a concentration of 600 mM.
Figure 10C:
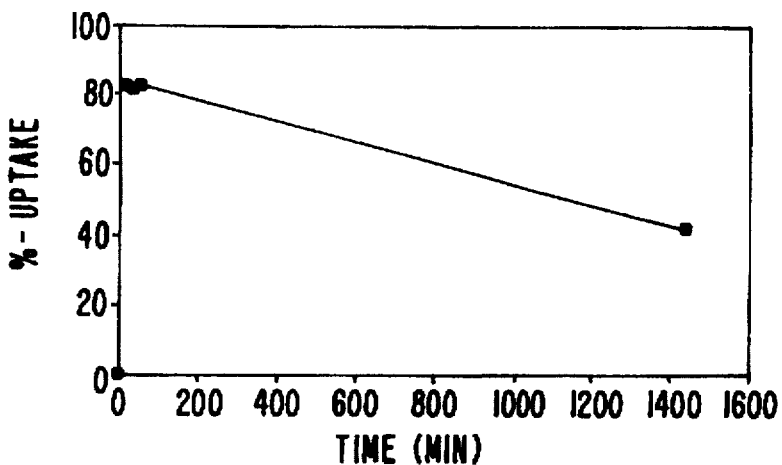
FIG. 10C shows drug retention characteristics of the loaded formulation from FIG. 10B over the 24 hours following loading.
Figure 11A:
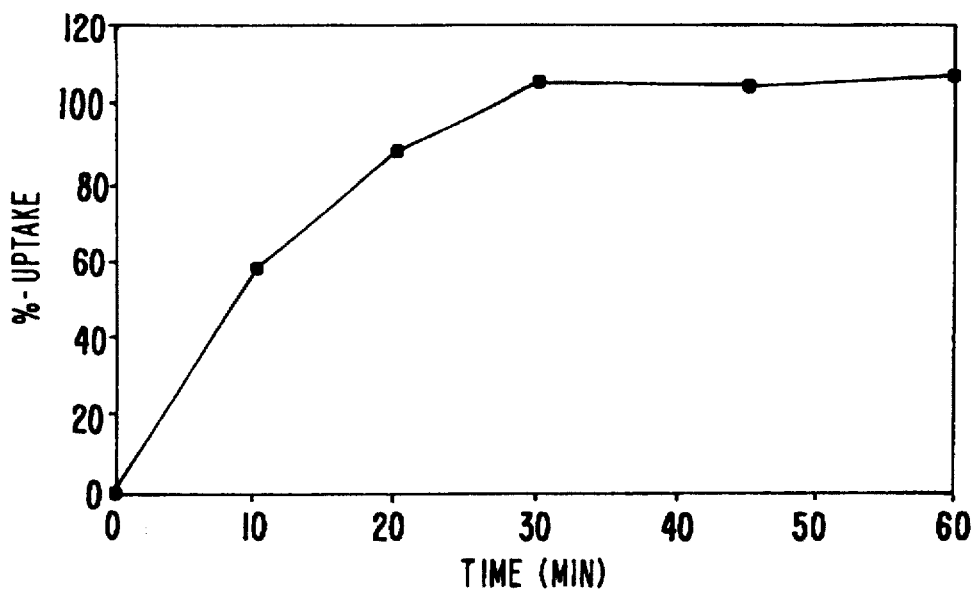
FIG. 11A depicts the uptake observed for doxorubicin at a drug to lipid ratio of 0.13 over approximately 30 minutes at 600 mM of MAC in DPPC/cholesterol vesicles at 45° C.

Doxorubicin, dissolved in saline, was added to the prepared egg phosphatidylcholine, DPPC/chol, or Sph/Cer/chol vesicles, and uptake was followed by removal and later analysis of aliquots for spin-column extraction. The uptake was performed at 25° C. for egg phosphatidylcholine LUVs (see FIG. 10A), and at 45° C. for the DPPC/cholesterol (see FIG. 11A) and Sph/Cer/cholesterol LUVs (see FIGS. 13 and 16). Ciprofloxacin, dissolved in water, was added to the prepared DPPC/chol, or DSPC/chol vesicles, and the uptake was performed at 45° C. (see FIG. 14) or 65° C. (see FIG. 15), respectively.

6.2 Effect of Counterion (sulfate vs. chloride)

Figure 13:
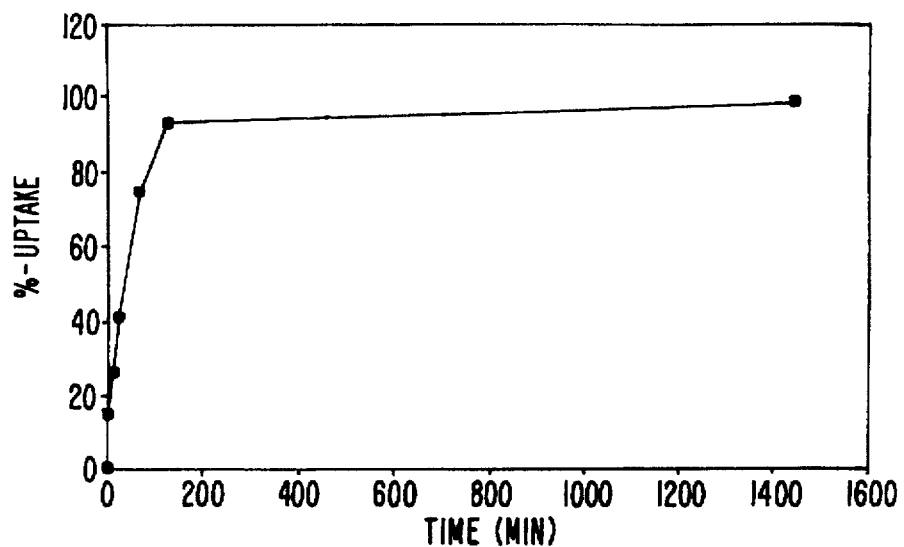
FIG. 13 shows the loading characteristics of doxorubicin into sphingomyelin/ceramide/cholesterol 4:1:4 (molar ration of Sph/Cer/cholesterol) LUVs of 200 nm prepared in 600 mM MAC. The temperature was 45° C. and the drug to lipid ratio was 0.36.
Figure 17:
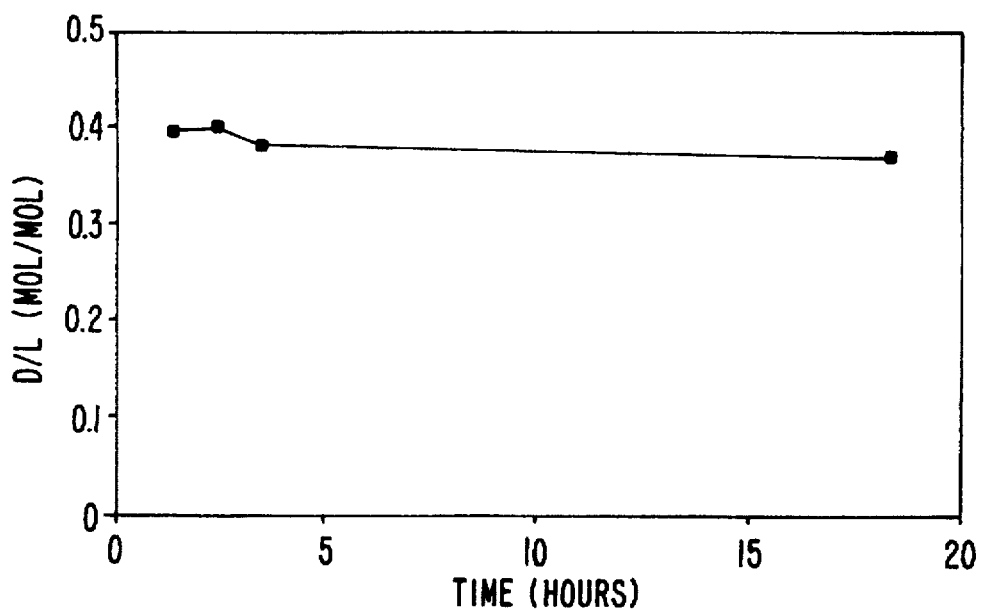
FIG. 17 is a graph showing the uptake of doxorubicin into Sph/Cer/cholesterol 1:1:1 (molar ratio) 100 nm LUVs containing Peg 2000Cer-C14 prepared in 300 mM MAC at 50° C., with an initial drug to lipid ratio of 0.66.

Doxorubicin uptake was also studied in LUVs composed of Sph/Cer/Chol using both MAC and MAS (FIGS. 13 and 17). Doxorubicin loaded at 45° C. into 200 nm Sph/Cer/Chol (4:1:4 molar ratio) LUVs prepared in 600 mM MAC took 2 hours to load with a starting drug to lipid ratio of 0.36. No drug had been lost from the lipid vesicles when measurements were taken 24 hours later.

Figure 14:
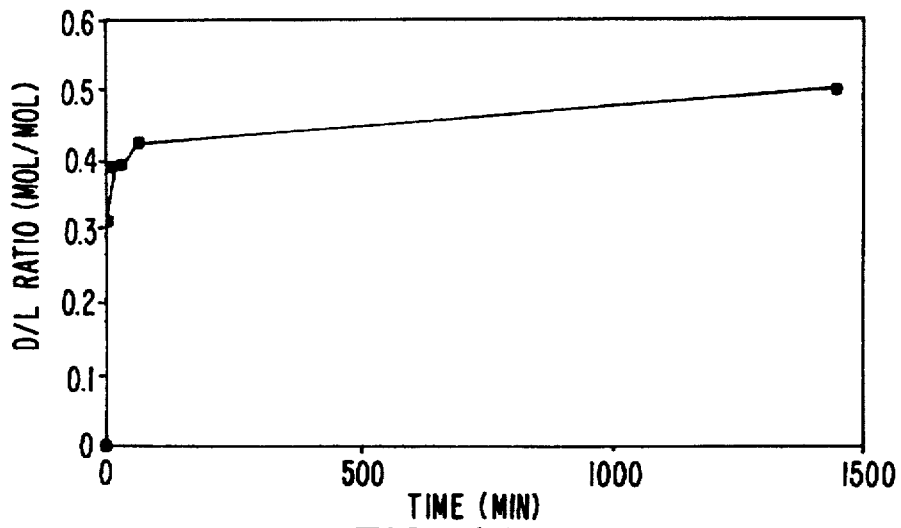
FIG. 14 illustrates the uptake of ciprofloxacin into 200 nm DPPC/cholesterol(55:45, mol:mol) LUVs in response to an internal concentration of 600 mM MAC at 45° C. for an initial drug to lipid (molar) ratio of 2.9.

Ciprofloxacin loaded at 45° C. into 200 nm DPPC/chol LUVs prepared in 600 mM MAC, starting with a drug to lipid ratio of 2.5 and incubated 15 minutes, resulted in a loaded drug to lipid ratio of 0.35 (see FIG. 14).

Figure 15:
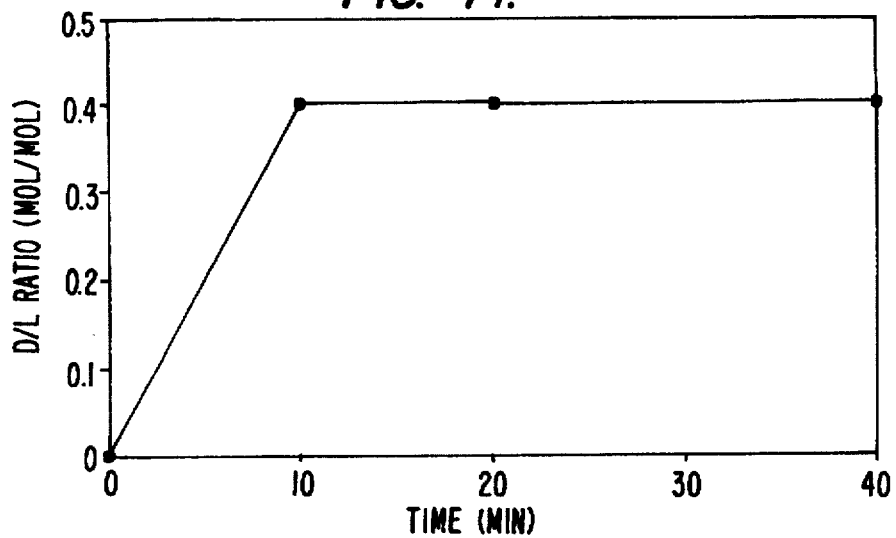
FIG. 15 shows the results of loading of ciprofloxacin into distearoylphosphatidylcholine/cholesterol 55:45 mol:mol (DSPC)/cholesterol 100 nm LUVs in response to a 300 mM $(CH_3NH_3)_2SO_4$ (MAS) gradient at 65° C. and with a drug to lipid ratio of 0.5. The final drug to lipid ratio was 0.4.

For DSPC/chol 100 nm LUVs prepared in 300 mM MAS, and incubated with an initial ciprofloxacin to lipid molar ratio of 0.5 and at a temperature of 65° C., a final drug to lipid ratio of 0.4 was achieved (see FIG. 15).

6.3 Effect of D/L

Figure 11B:
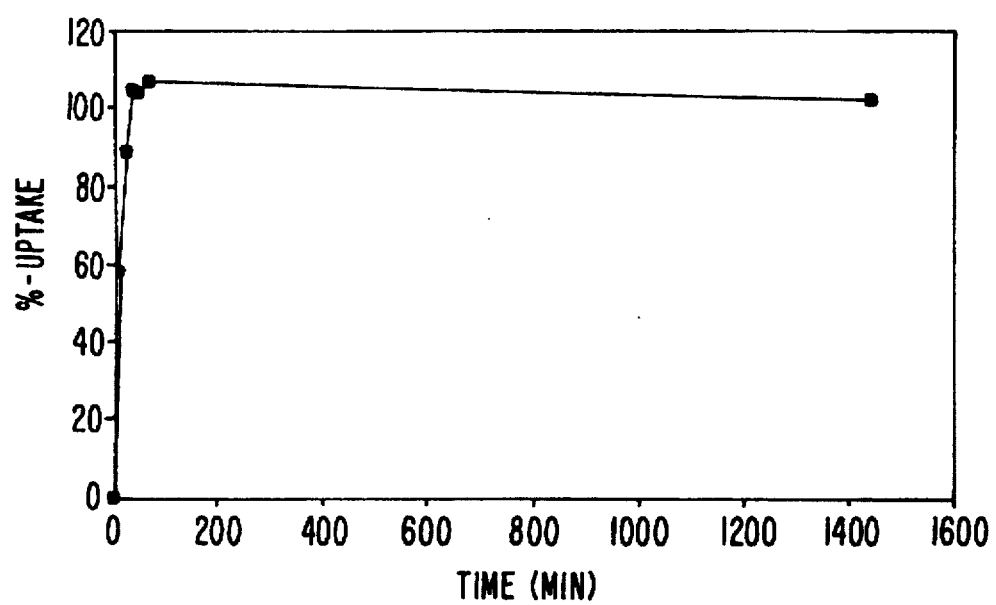
FIG. 11B is a graph showing drug retention over a period of 24 hours for the loaded formulation of FIG. 11A.

For a starting doxorubicin to lipid ratio of 0.13, essentially 100% uptake into 100 nm DPPC/chol (55:45 mol:mol) LUVs was observed after an incubation time of 30 minutes. The drug remained stably associated with the lipid for a period of 24 hours after which there were no further measurements (see FIGS. 11A and 11B).

Figure 12A:
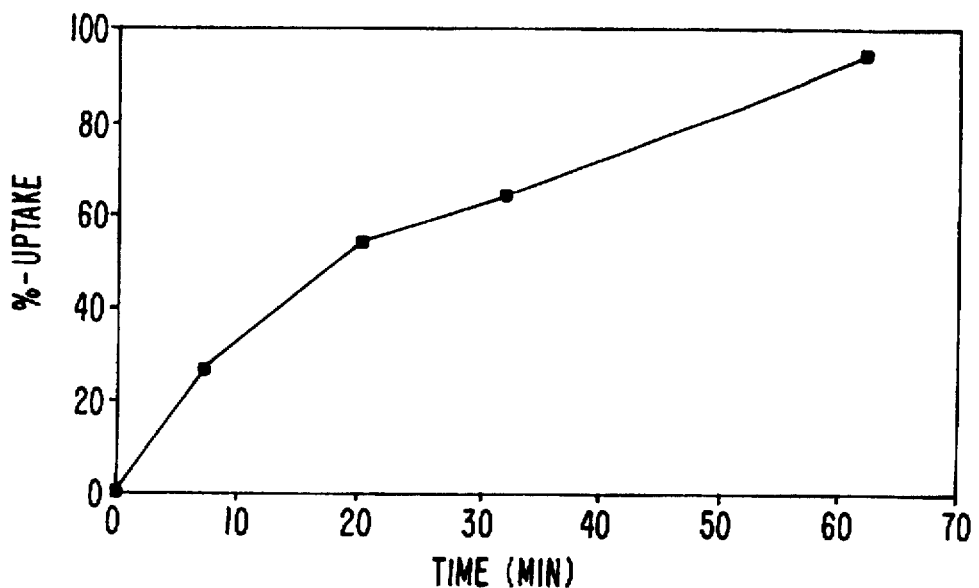
FIG. 12A illustrates the loading of doxorubicin obtained with 200 nm DPPC/cholesterol LUVs prepared in 600 mM MAC. The drug to lipid ratio was initially 0.25, and the temperature was 45° C.
Figure 12B:
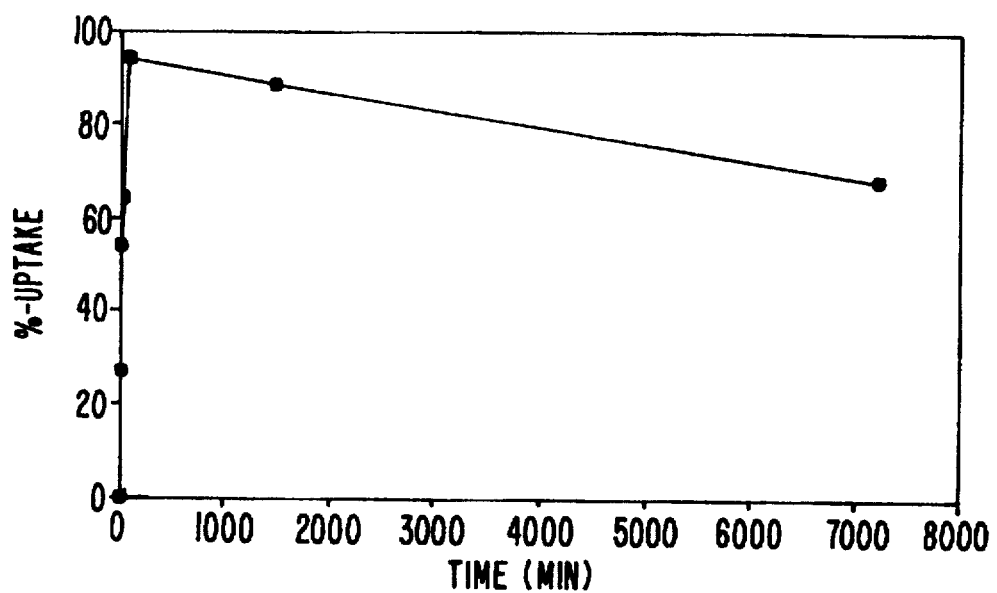
FIG. 12B is a graph showing the drug retention characteristics of the formulations of FIG. 12A.

For a starting drug to lipid ratio of 0.25 in 200 nm DPPC/Chol (55:45) LUVs, uptake at 45° C. took 60 minutes, and after 24 hours the retention was approximately 90%. At five days, the retention was 75% (see FIGS. 12A and 12B).

Figure 16A:
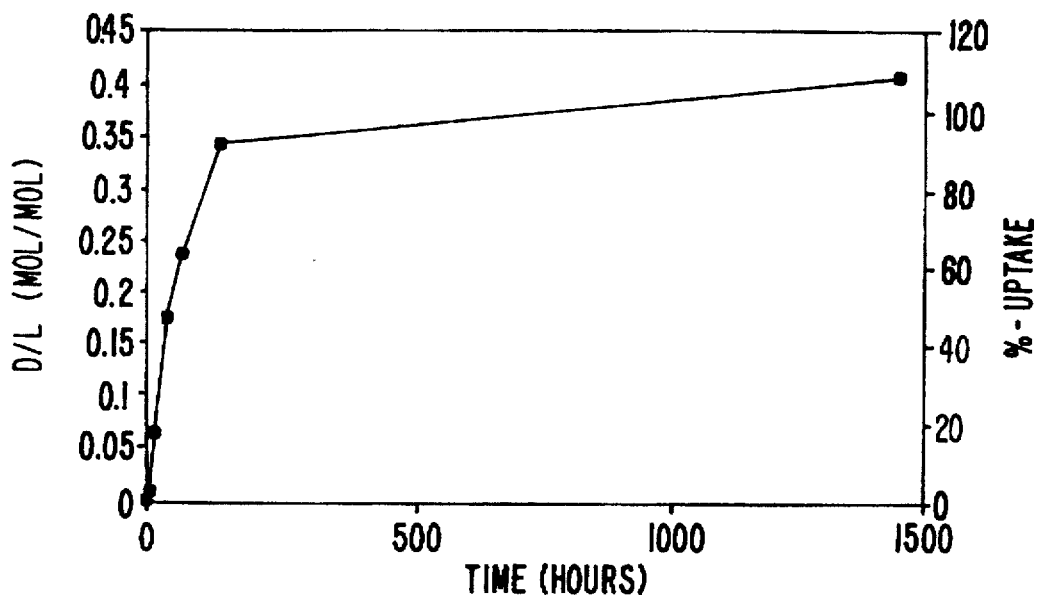
FIG. 16 illustrates the uptake of doxorubicin in DPPC/cholesterol (55:45 mol:mol) into 100 nm LUVs prepared in 300 mM MAS at 45° C., with initial drug to lipid ratios of 0.37 (FIG. 16A) and 1.2 (FIG. 16B).
Figure 16B:
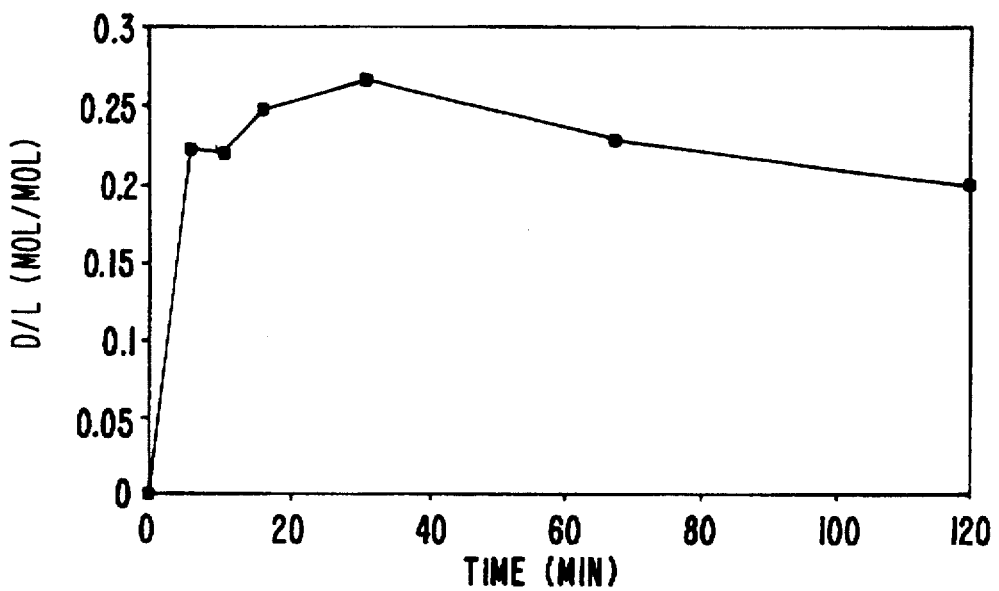

For an initial drug to lipid ratio of 0.37 in 100 nm DPPC/Chol (55:45) LUVs, essentially complete uptake at 45° C. occurred in 2 hours, and after 24 hours the retention was 100% (see FIG. 16A). This loading time could be reduced to about 30 min by raising the loading temperature to about 55° to 60° C. A drug to lipid ratio of 0.4 appears to be the maximum that can be achieved with a MAS concentration of 300 mM (see FIGS. 13, 15, 16A and 17). Increasing the initial drug to lipid ratio to 1.2 did not improve the loading, but rather appears to reduce the uptake of the drug, with a maximum drug to lipid ratio of 0.25 achieved after 30 min, followed by a decrease to approximately 0.2 over a period of 2 hours (see FIG. 16B). Very high external concentrations of DOX may affect the permeability of the membrane, making the preparation more leaky.

6.4 Effect of Lipid Vesicles with PEG conjugates

Doxorubicin uptake was studied in 100 nm LUVs composed of Sph/Cer/Chol (1:1:1 molar ratio) containing 5 mol % Peg2000Cer-C14 (polyethylene glycol derived ceramide with a 14 carbon fatty acyl chain—as described in co-assigned application 08/316,429 filed Sep. 30, 1994) to inhibit aggregation of the LUVs after extrusion. The formation of a MAS gradient and uptake of the drug were measured using aliquots taken and analyzed as described in EXAMPLE 2 above, except the initial drug to lipid ratio was 0.66 and the uptake was performed at 50° C. for one hour (FIG. 17). Note that a drug to lipid ratio of 0.4 was obtained in both FIGS. 13 and 17, similar to the maximum drug to lipid ratio obtained in DPPC/Chol LUVs.

The effect of variations in buffer and lipid composition was also examined for ciprofloxacin loading.

All results for the above experiments are presented in Table 1.

TABLE 1

| Lipid Composition (Molar Ratios) | Drug | Buffer | Size (nm) | Temp (°C.) | Initial molar ratio (D/L) | Final molar ratio (D/L) | Retention |
|---|---|---|---|---|---|---|---|
| Egg PC | DOX | MAC (300 mM) | 100 | RT | 0.26 | 0.11 (1 hr) | low |
| Egg PC | DOX | MAC (600 mM) | 100 | RT | 0.26 | 0.10 (24 hr) | 10× better |
| DPPC/Chol (55/45) | DOX | MAC (600 mM) | 100 | 45 | 0.13 | 0.13 (24 hr) | +++ |
| DPPC/Chol (55/45) | DOX | MAC (600 mM) | 200 | 45 | 0.25 | 0.22 and 0.17* | +++ |
| DPPC/Chol (55/45) | CIP | MAC (600 mM) | 200 | 45 | 2.9 | 0.5 (24 hr) | +++ |
| DSPC/Chol (55/45) | CIP | MAS (300 mM) | 100 | 65 | 0.5 | 0.4 (40 min) | +++ |
| DPPC/Chol (55/45) | DOX | MAS (300 mM) | 100 | 45 | 0.37 | 0.41 (24 hr) | +++ |
| DPPC/Chol (55/45) | DOX | MAS (300 mM) | 100 | 45 | 1.2 | 0.2 (2 hr) | ++ |
| Sph/Cer/Chol (4/1/4) | DOX | MAC (600 mM) | 200 | 45 | 0.36 | 0.35 (24 hr) | +++ |
| Sph/Cer/Chol (1/1/1) with PEG$_{2000}$ Cer-C14 | DOX | MAS (300 mM) | 100 | 50 | 0.66 | 0.37 (17 hr) | +++ |

*ratios are for 24 hr and 5 days, respectively.

EXAMPLE 7

This example illustrates the reduction in the rate of release of charged drugs from lipid vesicles using methylamine and pH gradients.

Lipid films of DSPC:chol:PEG2000 Cer-C20 and (N-(4-p-maleimidophyl)butyryl) distearoyl phosphatidylethanolamine (NWB-DSPE) (MPB available from Northern Lipids, Vancouver, Canada) (52:45:2:1) were hydrated in 300 mM MAS and freeze-thawed five times before extrusion (tenfold) at 65° C. through 100 nm filters. The lipid vesicles were then passed down a PD-10 gel filtration column (prepacked Sepharose column available from Pharmacia) equilibrated with saline. The remaining lipid vesicles were incubated with $^{14}$C-labeled doxorubicin in a mole ratio of 0.2 parts drug to 1 part lipid. Both lipid and $^{14}$C-doxorubicin were heated separately at 60° C. for 5 minutes before mixing together. After mixing, the combination was held at 60° C. for 10 more minutes to allow full drug uptake.

Figure 18:
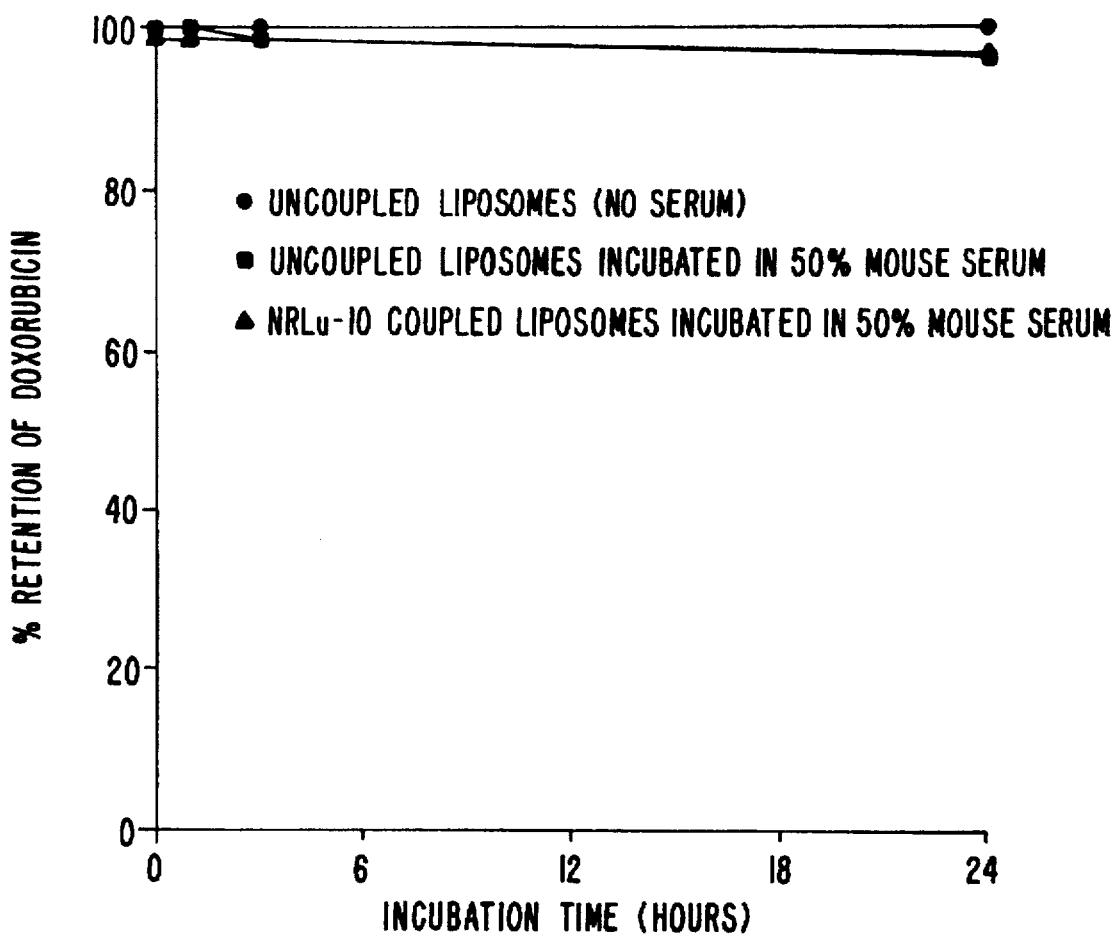
FIG. 18 shows the retention characteristics exhibited by liposomes loaded with doxorubicin into DSPC/Cholesterol +2% Peg2000er-C20+1% N-(4-p-maleimidophenyl) butyryl)phosphatidylethanolamine MPB-PE) lipid vesicles using a 300 mM methylammonium sulfate gradient. The three curves show lipid vesicles (circles), lipid vesicles preincubated in 50% mouse serum (squares), and antibody-coupled lipid vesicles incubated 50% mouse serum (triangles).

The loaded lipid vesicles were separated and then incubated 24 hours in either Hepes Buffered Saline (HBS) at pH 7.5 or an equal volume of 50% mouse serum. After 1, 4 and 24 hours, aliquots were taken and passed down a spin column to separate the LUVs from the free $^{14}$C-doxorubicin. Results are presented in FIG. 18.

EXAMPLE 8

This example illustrates the reduction in the rate of release of charged drugs from antibody-coupled lipid vesicles using a methylamine gradient.

Loaded lipid vesicles prepared as described in Example 4 above were coupled with NRLU-10 antibody. Antibody was modified with the heterobifunctional crosslinking agent N-succinimidyl-3-(2-pyridyldithiopropionate) (SPDP—available from Pierce, Rockford, Ill., USA) and then activated with dithiothreitol (DTT). The resulting activated antibody was mixed with the liposomes at a ratio of 75 µg antibody to each µM lipid. After a 16 hour coupling reaction, the lipid vesicles were passed down a CL-4B column to remove unreacted antibody. The final immunoliposome preparation contained 38.7 µg antibody/µmole lipid.

The coupled lipid vesicles were incubated for 24 hours in 50% mouse serum. After 1, 4 and 24 hours, aliquots were taken and passed down a spin column to separate the loaded liposomes from the $^{14}$C-doxorubicin that has leaked out. A full 98.6% of the labeled doxorubicin was retained in the lipid vesicles (see FIG. 18).

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method of preparing a liposome formulation of a zwitterionic quinolone antibacterial agents, said method comprising;

(i) preparing a mixture of liposomes in an aqueous solution, said liposomes having an encapsulated medium and an external medium, wherein said encapsulated medium and said external medium each contain a methylammonium salt;

(ii) establishing a concentration gradient of methylamine across the liposome membranes by removing or diluting said methylammonium salts in said external medium; and (iii) incubating said liposomes of step (ii) with said zwitterionic agents, said zwitterionic agents being present in a neutral form which is attracted toward said encapsulated medium of said liposomes by said concentration gradient of methylamine, for a period of time sufficient to cause adherence of said therapeutic agent to said liposomes.

2. A method in accordance with claim 1 wherein multiple zwitterionic agents are loaded into said liposome.

3. A method in accordance with claim 1 wherein said zwitterionic agent is ciprofloxacin.

4. A method in accordance with claim 1, wherein said liposome formulation comprises liposomes prepared from mixtures selected from the group consisting of egg phosphatidylcholine, dipalmitoylphosphatidylcholine/cholesterol, and sphingomyelin/ceramide/cholesterol.

5. A method in accordance with claim 1, wherein said liposome formulation comprises liposomes prepared from distearoylphosphatidylcholine/cholesterol, said zwitterionic agent is ciprofloxacin, and a drug-to-lipid ratio of 0.4 is achieved.

6. A method of treating a mycobacterial infection in a host comprising administering to said host a liposome formulation of a zwitterionic quinolone antibacterial agent prepared according to the method of claim 1.

7. A method in accordance with claim 6, wherein said antibacterial agent is ciprofloxacin.

8. A liposomal formulation of a zwitterionic quinolone antibacterial agent prepared according to the method of claim 1.

9. A liposomal formulation in accordance with claim 8 wherein said zwitterionic quinolone antibacterial agent is ciprofloxacin.

10. A method of retaining a zwitterionic quinolone antibacterial agent in a liposome formulation, said method comprising;

(i) preparing a mixture of liposomes in an aqueous solution, said liposomes having an encapsulated medium and an external medium, wherein said encapsulated medium contains a methylammonium salt and said zwitterionic agent; and (ii) establishing a concentration gradient of methylamine across the liposome membranes, wherein said gradient results in said encapsulated zwitterionic agent becoming protonated and thereby retained in said liposome formulation.

11. A method in accordance with claim 10 wherein said methylammonium salt is selected from the group consisting of methylammonium chloride and methylammonium sulfate.

12. A method in accordance with claim 10 wherein said zwitterionic agent is ciprofloxacin.

* * * * *